United States Patent [19]
Orsak et al.

[11] Patent Number: 6,162,223
[45] Date of Patent: Dec. 19, 2000

[54] DYNAMIC WRIST FIXATION APPARATUS FOR EARLY JOINT MOTION IN DISTAL RADIUS FRACTURES

[75] Inventors: James E. Orsak, Huntersville, N.C.; David L. Evans, Bartlett, Tenn.

[73] Assignee: Smith & Nephew, Inc., Memphis, Tenn.

[21] Appl. No.: 09/289,358

[22] Filed: Apr. 9, 1999

[51] Int. Cl.[7] ................................. A61B 17/56
[52] U.S. Cl. .............................................. 606/59
[58] Field of Search .................. 606/53, 54, 57, 606/59, 55; 623/21

[56] References Cited

U.S. PATENT DOCUMENTS

| | | | |
|---|---|---|---|
| 1,789,060 | 1/1931 | Weisenbach | 606/54 |
| 1,997,466 | 4/1935 | Longfellow | 606/59 |
| 2,251,209 | 7/1941 | Stader | 606/59 |
| 2,372,866 | 4/1945 | Tofflemire | 606/54 |
| 4,483,334 | 11/1984 | Murray . | |
| 4,628,919 | 12/1986 | Clyburn | 606/55 |
| 4,696,293 | 9/1987 | Ciullo | 606/57 |
| 4,895,141 | 1/1990 | Koeneman et al. | 606/54 |
| 4,969,886 | 11/1990 | Cziffer et al. | 606/59 |
| 5,122,140 | 6/1992 | Asche et al. | 606/55 |
| 5,207,676 | 5/1993 | Canadell et al. . | |
| 5,219,349 | 6/1993 | Krag et al. . | |
| 5,429,637 | 7/1995 | Hardy . | |
| 5,443,465 | 8/1995 | Pennig . | |
| 5,620,442 | 4/1997 | Bailey et al. | 606/54 |
| 5,653,707 | 8/1997 | Taylor et al. | 606/54 |
| 5,683,389 | 11/1997 | Orsak | 606/59 |
| 5,803,924 | 9/1998 | Oni et al. | 606/54 |
| 5,941,877 | 8/1999 | Viegas et al. | 606/55 |
| 5,976,133 | 11/1999 | Kraus et al. | 606/54 |

*Primary Examiner*—Gene Mancene
*Assistant Examiner*—Eduardo C. Robert
*Attorney, Agent, or Firm*—Garvey, Smith, Nehrbass & Doody, LLC

[57] ABSTRACT

A joint fixator apparatus conforms to the natural axis of rotation of the joint in question, such as a patient's wrist or knee to avoid the possibility of bone fragment displacement and/or fracture reduction. The apparatus includes two fixation rod sections or shaft sections with a spring module therebetween. The spring module is in the form of a flexible coupler that connects to respective ends of the external fixator rod. The module can include a removable clip to restrain the motion of the spring a desired amount such as before healing takes place. The rods can be used to hold pin clamps which then hold bone pins for attachment to selected bones of the patient such as above and below a joint or above and below a fracture. The pin clamps can be moved along the rod sections to provide distraction of the joints for a ligamentotaxis effect in reducing the fracture.

37 Claims, 6 Drawing Sheets

DYNAMIC WRIST FIXATION APPARATUS FOR EARLY JOINT MOTION IN DISTAL RADIUS FRACTURES

CROSS-REFERENCE TO RELATED APPLICATIONS

Not applicable.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to orthopaedic fixation devices, and more particularly to an improved dynamic wrist fixator module that uses a flexible coupler for connecting two external fixation rods. The module also contains a movable clip to restrain the motion of the coupler. The apparatus can be used to hold pin clamps which support bone pins for attachment to the bone parts.

2. General Background of the Invention

One of the preferred methods of treating bone fractures such as distal radius fractures is to reduce the fracture by distracting the surrounding ligaments with an external fixation device. This technique is known as ligamentotaxis. With this method, the wrist is immobilized for six to eight weeks until healing is complete.

One problem with leaving the wrist immobilized for long periods of time is the possibility of wrist stiffness or cartilage deterioration due to poor joint nutrition. A joint relies on movement to allow the fluids to bathe the cartilage and provide a proper environment for the joint.

Some of the existing external fixators address this issue by providing some joint motion. However, the existing designs constrain the fixator to certain axes of rotation which must be properly aligned with the anatomical axis of wrist or joint motion. Since it is very difficult to align the fixator with the exact axis of joint movement, there is often a mismatch between the fixator axis and the joint axis which can result in the displacement of the bone fragment and loss of fracture reduction. This displacement results from the wrist being forced to move about the axis of the fixator which goes against its normal movement.

An example of a technique of multi-planar ligamentotaxis is described by Dr. John Agee in an article published in *Orthopaedic Clinics Of North America*, Vol. 24, No. 2, April 1993 and entitled "External Fixation: Technical Advances Based Upon Multi-Planar Ligamentotaxis". John Agee is also the named patentee of the U.S. Pat. Nos. 4,548,199; 4,611,586; and 4,922,856. The fixator developed by Dr. Agee provides a method of achieving multi-planar ligamentotaxis through gradual turning of worm screws.

Several fixation systems have been patented that relate to the bone segments. An example is U.S. Pat. No. 4,483,334, issued to William Murray and entitled "External Fixation Device". The '334 patent discloses a device for holding bone segments in known relation to each other. The apparatus includes a pair of bone clamp assemblies each secured to bone pins extending from the bone segments. A bridge extends between the pin clamp assemblies and a specialized high friction universal assembly connects the bridge to each of the pin clamp assemblies.

U.S. Pat. No. 5,207,676, issued to Jose Canadell et al., relates to an external fixator with controllable damping. This external fixator disclosed in the '676 patent is for the correction and reduction of bone fragments. The apparatus comprises a bar fastened to a biocompression system on which the bar and system are disposed upon supports for fastening pins inserted into bones.

A spinal fixator reduction frame is the subject of U.S. Pat. No. 5,219,349. A reduction frame disclosed in the '349 patent is secured to shaft handles extending from the pedicle screws of a Vermont Spinal Fixator type implant. Shaft clamps secure two T-handles of the reduction frame to the shaft handles. A lower-rod assembly joins the two opposite T-frames by means of lower-rod clamps. The shaft clamps are provided with four degrees of freedom. The joint between the lower-rod assembly and T-handle is provided with five degrees of freedom. The lower-rod assembly and the T-handle are provided with power screw threads to allow for precise translational control. The shaft clamps and lower-rod clamps are provided with taper fit joints to allow for infinite rotational adjustment and fixture. An upper-rod assembly is also provided on the T-handles to produce rotation of the T-handles by providing means for changing the distance between the upper ends of the T-handles. Finger grips are provided on the upper-rod assembly to allow the surgeon to easily use one hand to either apply or monitor the force acting along the upper-rod.

The Hardy U.S. Pat. No. 5,429,637, discloses an external modular fixator for immobilization of a fracture. The apparatus includes elements functioning as clamps and receiving anchor pins to be fixed in a predetermined angular position on either side of a fracture. A mobilization relay body is configured to be attached to the fracture. The mobilization body has a device for locking which is used to lock the clamps. A fixator and the mobilization relay bodies are lockable in various chosen arrangements. The device is shown affixed to a patient's lower arm and wrist area.

The Pennig U.S. Pat. No. 5,443,465 refers to an osteosynthesis aid which is used in particular for the fixation of a pelvis and includes a central body which is formed of at least two arm or link members, each of which has an elongated slot through which a lock bolt is passed to provide a releasable clamped joint and each of which also has releasably secured ball-joint connection to an end-connecting clamp for bone-pin or bone-screw anchorage to an afflicted bone.

A Russian Patent SU 1491-492-A1 discloses a femur neck fracture osteosynthesis device that has a support in the form of plates with inclined slots for pins. The plates have apertures for pin locks. The pin locks are designed in the form of threaded rods with nuts and washers. The plates are in parallel plane with an offset greater than the sum of the thickness of the plates and the pin diameter. The plates are interconnected by connecting pieces. Pins are passed after passing through the aiming pin and are locked by the pin locks. This device has an advantage of simplifying the design by allowing crossing-over angle in the planes parallel with the femur axis.

BRIEF SUMMARY OF THE INVENTION

The present invention provides a fixator apparatus that conforms to the natural axis of rotation of the joint (e.g., wrist) to avoid the possibilities of bone fragment displacement and/or loss of fracture reduction.

The present invention includes a spring module that is a flexible coupler that connects to external fixation rods. In one embodiment, the module also contains a removable clip to restrain the motion of the spring a desired amount.

The rods are used to hold pin clamps which hold bone pins for attachment to the selected bones. The pin clamps can be moved along the rod sections to provide distraction of the joint for a ligamentotaxis effect in reducing the fracture.

The spring module of the present invention can be rigidly fastened to the rods with set screws and the module positioned at the approximate location of the anatomical center of wrist movement near the base of the capitate bone.

The flexible spring module can be pre-compressed and held in place with a locking clip. After initial bone healing has occurred in three to four weeks, the clip can then be removed and the wrist freed to move. The pre-compression in the spring counters the tension force from the ligamentotaxis to prevent loss of distraction. In addition, the hemispherical ends of the rods will allow flexion of the wrist while maintaining contact with each other to prevent loss of distraction and length. Since the spring can flex about a variable of center of rotation, it will conform to the natural movement of the joint (e.g., wrist). As the patient moves the wrist during mobilization, the patient will have to overcome the spring force, which will attempt to return the wrist to the initial spring position (see FIGS. 6, 11 and 12). This spring also provides exercise for the wrist.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
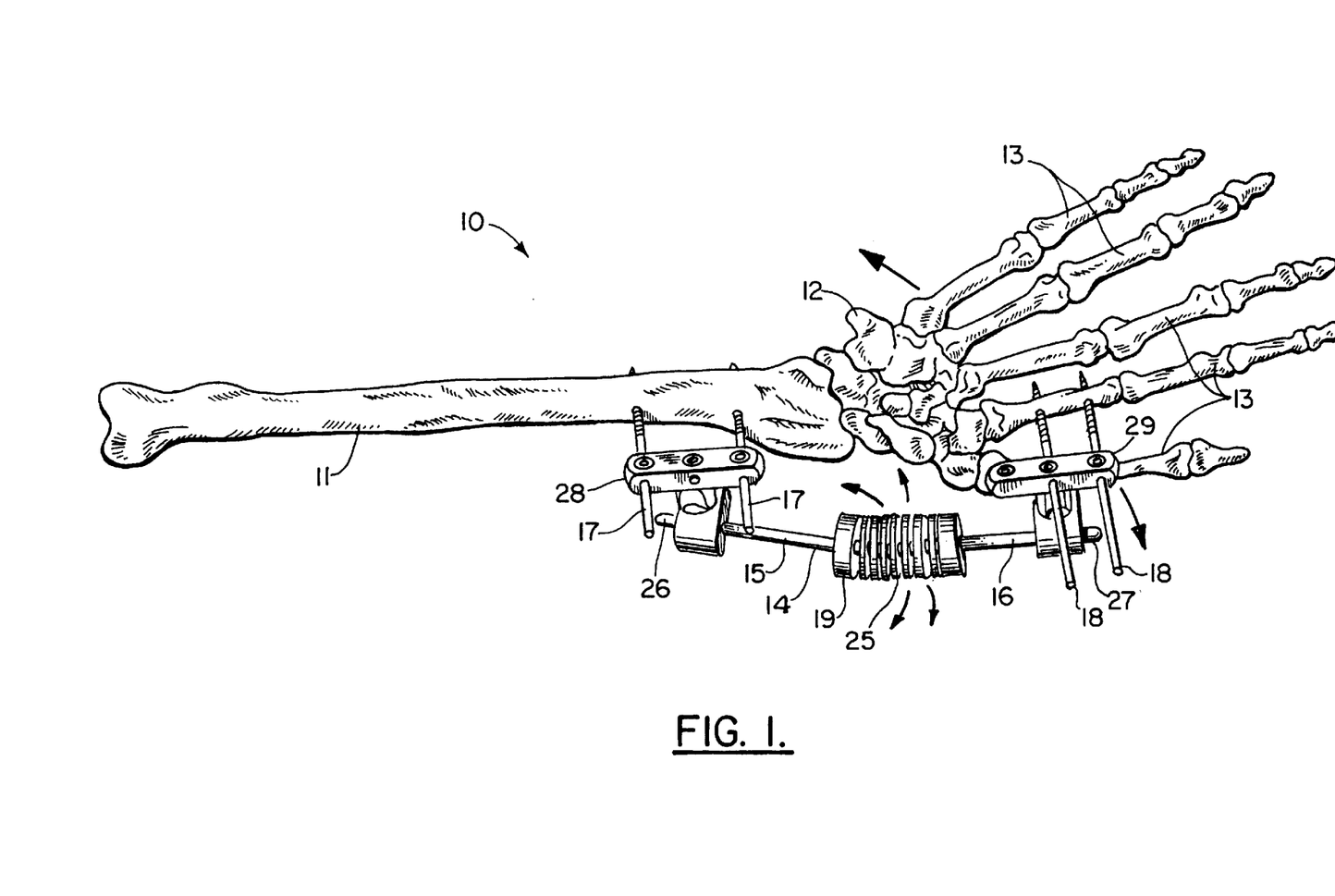
FIG. 1 is a perspective view of the preferred embodiment of the apparatus of the present invention.

FIGS. 1–5 show generally the preferred embodiment of the apparatus of the present invention designated generally by the numeral 10 in FIG. 1. Fixation apparatus 10 is shown attached to a patient's arm, wrist, and hand as a wrist fixator. In FIG. 1, the patient's radius 11, wrist 12, and metacarpals 13 are shown.

The apparatus 10 of the present invention could be used for other joints such as knee, ankle, elbow, hip, shoulder or finger. The fixation apparatus 10 includes a rod 14 having a proximal rod section 15, a distal rod section 16, and a flexible spring module connector member 19.

Figure 2:
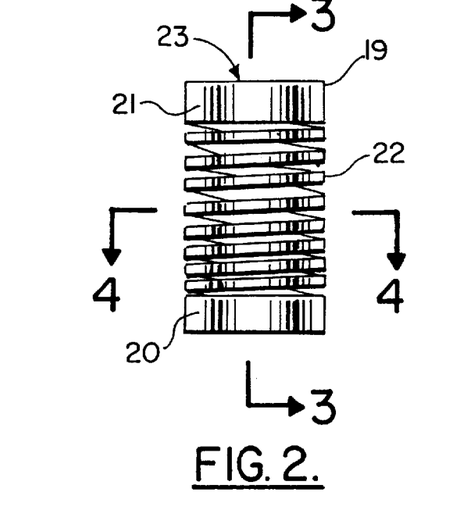
FIG. 2 is a fragmentary view of the preferred embodiment of the apparatus of the present invention illustrating the spring coupler portion thereof.
Figure 3:
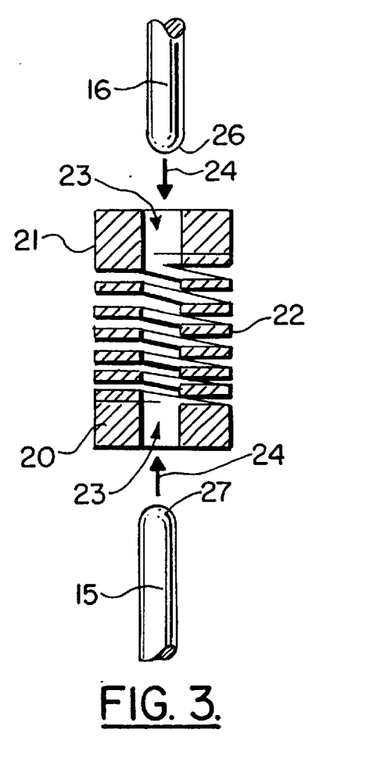
FIG. 3 is a sectional view taken along lines 3—3 of FIG. 2.
Figure 4:
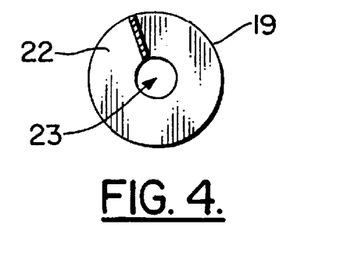
FIG. 4 is a sectional view taken along lines 4—4 of FIG. 2.
Figure 6:
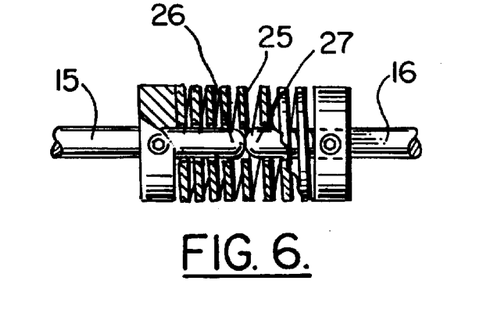
FIG. 6 is a fragmentary view of the preferred embodiment of the present invention illustrating the connection of flexible spring module and rod ends.
Figures 11, 12, 13, 14, 15:
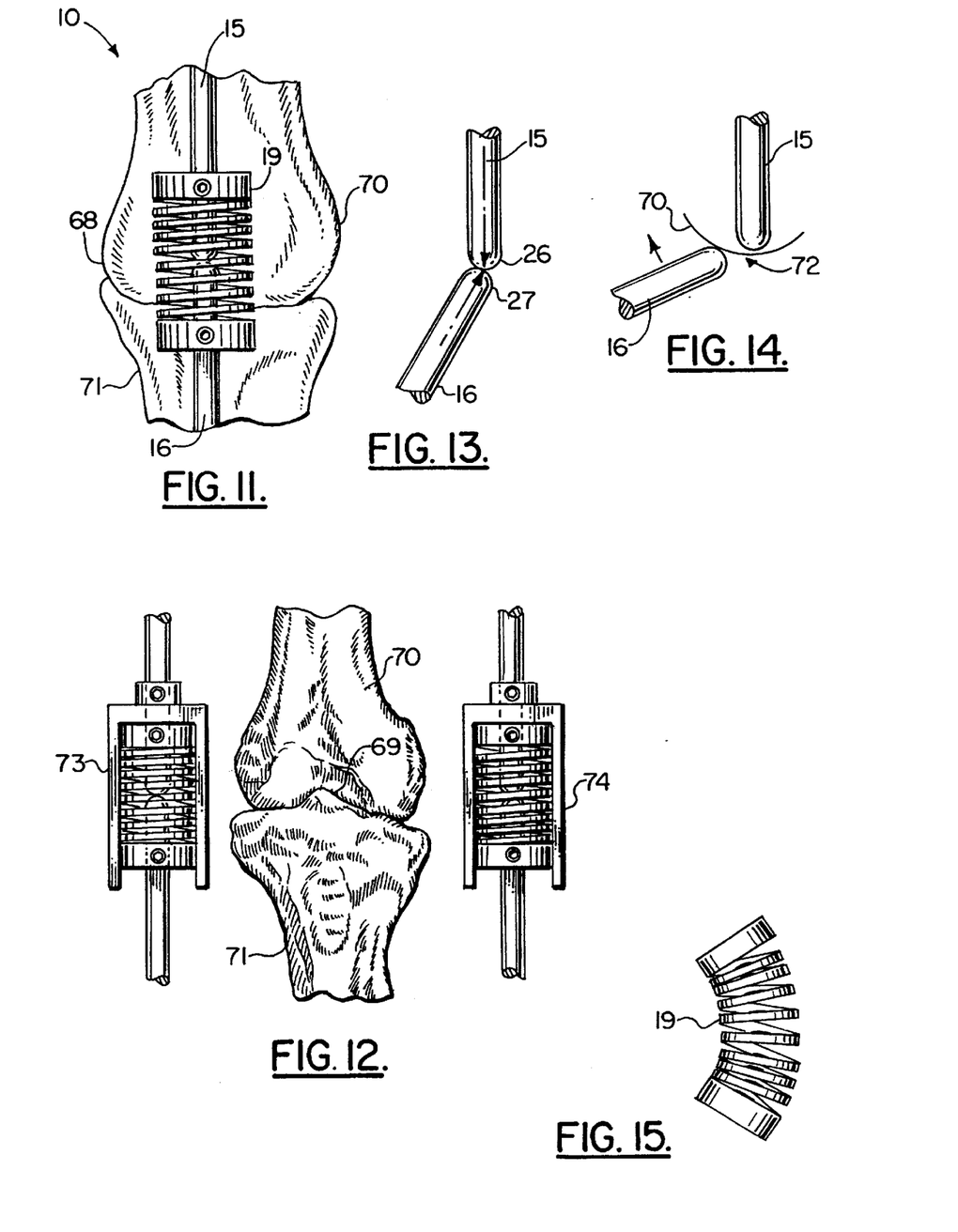
FIG. 11 is a side fragmentary view of the preferred embodiment of the apparatus of the present invention illustrating its use as a fixator at a patient's knee wherein the flexible shaft coupler and two rod end portions are illustrated.
FIG. 12 is a frontal view of the flexible shaft couplers and rod end portions positioned on opposite sides of a patient's knee.
FIG. 13 is a partial side view of the preferred embodiment of the apparatus of the present invention illustrating shaft position when used as a knee hinge with variable center of rotation.
FIG. 14 is a partial side view of the preferred embodiment of the apparatus of the present invention illustrating shaft position when used as a knee hinge with a variable center of rotation and wherein the shaft or rods move apart at larger flexion angles.
FIG. 15 is a side fragmentary view of the preferred embodiment of the apparatus of the present invention illustrating the flexible shaft coupler portion to show that it will expand to follow the knee through its range of motion.

A pair of proximal bone pins 17 are attached to the patient's radius 11. A pair of distal bone pins 18 are attached to one or more of the patient's metacarpals 13. A proximal clamp 28 forms an interface between the proximal bone pin 17 and the rod 14 at proximal rod section 15. Distal clamp 29 forms an interface between distal bone pins 18 and the rod 14 at distal rod section FIGS. 2–4 show more particularly the construction of flexible rod connector member 19. Rod connector member 19 includes a pair of cylindrically-shaped end portions including cylindrical proximal end 20, distal end 21 and a central spring section 22. Each of the end portions 20, 21 has a cylindrically-shaped open center that forms a part of cylindrically-shaped elongated bore 23 in FIG. 3. The bore 23 elongates, angulates, and/or changes in shape when the flexible spring module connector member 19 flexes, extends, and angulates as shown in FIGS. 1, 6, and 15.

Coil spring section 22 extends between cylindrical proximal end 20 and cylindrical distal end 21 as shown in FIGS. 2 and 3. Arrows 24 in FIG. 3 illustrate that the rod sections 15 and 16 (and more particularly the hemispherical end portions 26, 27 thereof) are inserted into bore 23 until they meet (se FIG. 6). End portions 26, 27 meet at the contact point 25, that is shown in FIGS. 1, 6, and 11–12. In FIGS. 1–11 and 13, the rod member end portions 26, 27 abut and engage even when the rod members 15, 16 angulate to form an obtuse angle.

Figure 5:
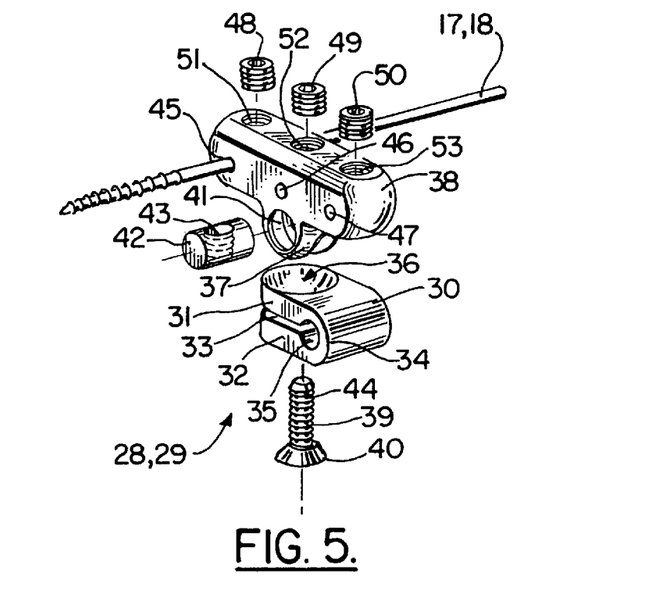
FIG. 5 is a perspective view of a clamp for use with the fixation apparatus of the present invention.

In FIG. 5, the construction of clamps 28, 29 are shown more particularly. Each clamp 28, 29 can be a universally adjustable, articulating clamp as shown in FIG. 5. Clamps 28, 29 are more particularly shown and described in copending prior patent application Ser. No. 08/349,323, filed Dec. 5, 1994 incorporated herein by reference. Each clamp apparatus 28, 29 includes a clamp body 30 that includes a pair of flanges 31, 32 with a gap 33 therebetween. The flanges 31, 32 have a gap 33 therebetween, but are connected together with C-shaped portion 34 of clamp body 30.

A cylindrically-shaped transverse bore 35 is provided at C-shaped member 34 as shown in FIG. 5. An opening 36 extends through both flanges 31 and 32. At flange 31, the opening 36 is hemispherically shaped to conform to the shape of hemispherical projection 37 of pin body 38. At flange 32, the opening 36 has a countersunk portion for receiving the head 40 of set screw 39.

Pin body 38 includes a transverse, cylindrically-shaped bore 41 at hemispherically-shaped projecting portion 37. The bore 41 receives a cylindrically-shaped nut 42 having an internally threaded bore 43 that connects with the threaded shaft 44 of set screw 39 upon assembly. The cylindrically-shaped bore 35 conforms to the outer surface of rod section 15 or 16 as shown in FIGS. 1 and 5. The bore 35 is preferably cylindrically shaped and of uniform diameter so that it conforms to the outer surface of cylindrical rod sections 15 and 16 so that clamp 28 or 29 can slide between the hemispherical ends 26 or 27 and connector 19.

Pin body 38 includes a plurality of pin holding openings 45, 46, 47 that can hold a bone pin 17 or 18. Set screws 48, 49, 50 register in correspondingly-shaped internally threaded openings 51, 52, 53 so that when the set screws 48, 49, 50 are tightened, they hold the bone pin 17 or 18 in a selected position. In FIG. 1, the clamp 28 holds two bone pins 17 at pin bores 45, 47 while the pin bore 46 is empty. In FIG. 1, the clamp 29 holds two bone pins 18 at pin bores 45 and 46 while the bore 47 is empty.

Figure 7:
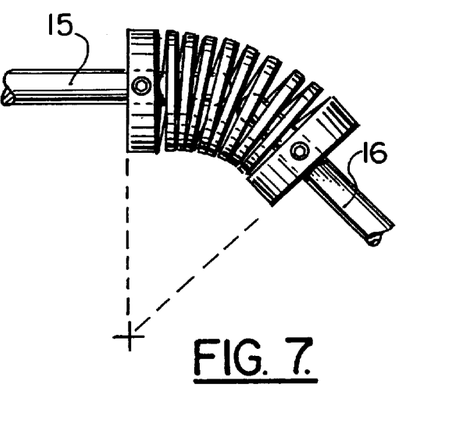
FIG. 7 is a fragmentary view of the preferred embodiment of the apparatus of the present invention showing the flexible spring coupler module in use with a patient's wrist joint.

FIGS. 6–7 show the position of rod ends 26, 27 upon assembly to flexible shaft coupler 19 during use. The hemispherical rod ends 26, 27 make contact at 25 to prevent loss of distraction of the wrist joint so that the length of the radius is maintained. In FIG. 13, the rod ends 26, 27 typically maintain contact when the connector 19 is flexed and with respect to the knee joint fixator shown in FIGS. 11–15.

Figure 8A:
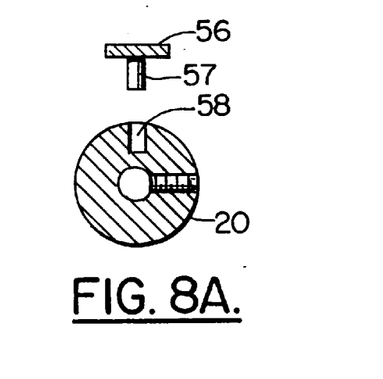
FIGS. 8A–8B are schematic end and side views of the preferred embodiment of the apparatus of the present invention.
Figure 8B:
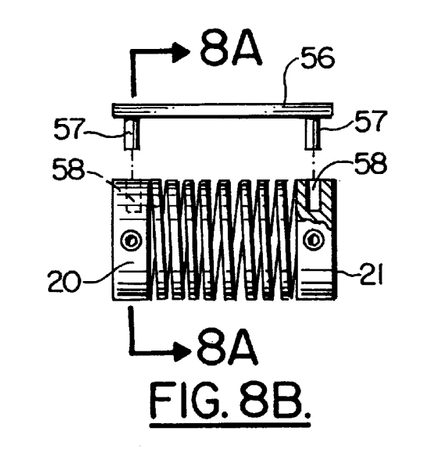

In FIGS. 8A–8B, a fixed spring compressor is shown that is comprised of a beam 56 having a pair of opposed tabs 57 extending from beam 56 at generally right angles. The tabs 57 fit correspondingly shaped sockets 58 on coupler 19 at its cylindrical end portions 20, 21. The bore 23 of coupler 19 can optionally be a hexagonally-shaped bore 59 that can be used with rods 15, 16 that are hexagonally shaped rather than cylindrically shaped.

Figure 9:
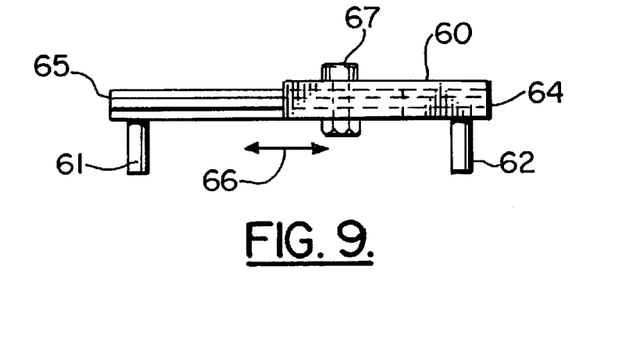
FIGS. 9 and 10 are side and end views respectively of a flexible spring compressor useful with the spring coupler of the present invention shown in FIGS. 1–8B.
Figure 10:
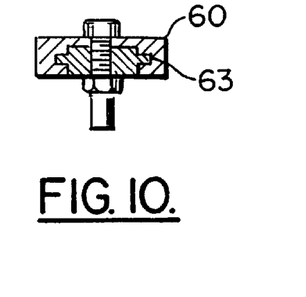

FIGS. 9 and 10 show an adjustable spring compressor 60. The spring compressor 60 has tabs 61, 62 that fit the sockets 58 of coupler 19 in FIGS. 8A–8B. However, in FIGS. 9 and 10, the compressor is adjustable providing telescoping sections 64, 65. The larger section 64 has a slot 63 that receives the section 65 in telescoping fashion as indicated by the arrow 66 in FIG. 9. A bolted connection 67 can be used to affix the section 64, 65 together in a selected position so that the tabs 61, 62 can hold the spring coupler 19 in a desired compressed position.

In FIGS. 11–15, the fixation apparatus 10 of the present invention can be used for fixating a patient's knee 68 while allowing the knee to flex through its normal range of motion. In FIGS. 11–12, the flexible shaft coupler 19 is shown being positioned adjacent interface 69 between the patient's distal femur 70 and proximal tibia 71. Guides 73, 74 can be used to prevent the coupler 19 from bending to the medial or lateral side.

In FIGS. 13 and 14, the rod sections 15, 16 are shown maintaining contact at their hemispherical ends 26, 27 respectively when the leg is slightly flexed. However, the end portions 26, 27 move apart at larger flexion angles with a gap 72 therebetween as shown in FIG. 14.

FIG. 15 illustrates the coupler 19 during such flexion of the knee to show that the coupler 19 expands to follow the knee through its range of motion providing a variable center of rotation.

Figure 16:
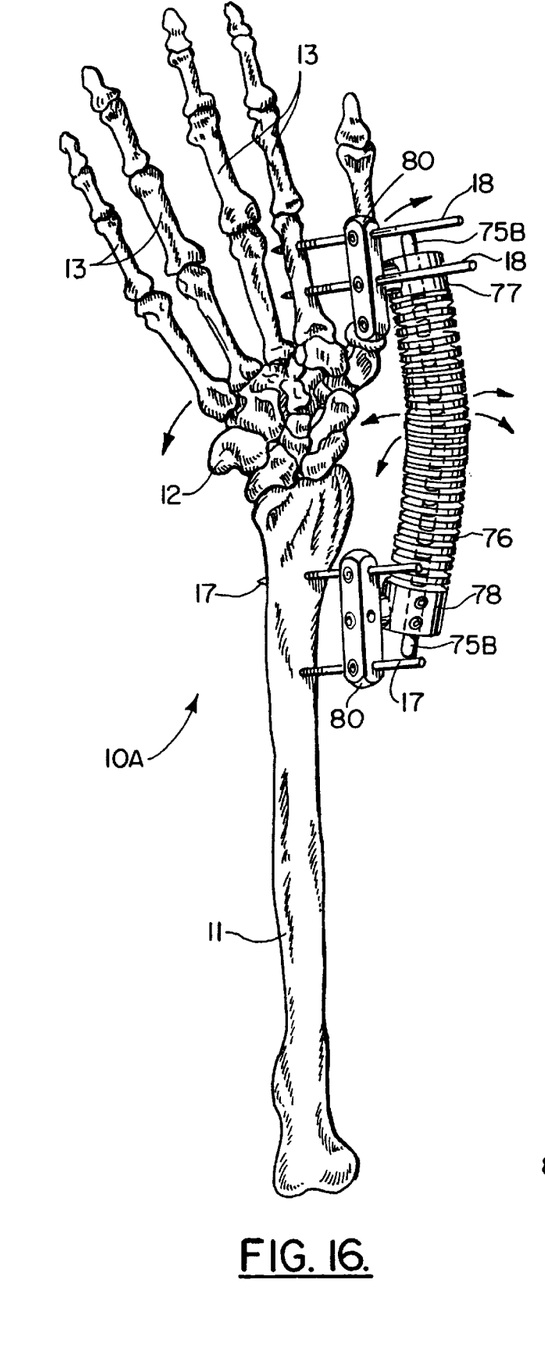
FIGS. 16–17 are perspective view of an alternate embodiment of the apparatus of the present invention.
Figure 17:
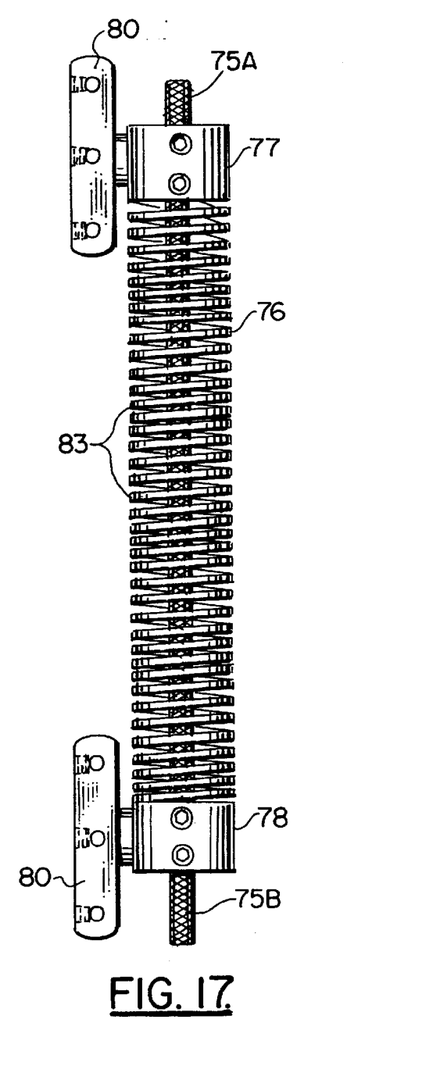
Figures 18, 20:
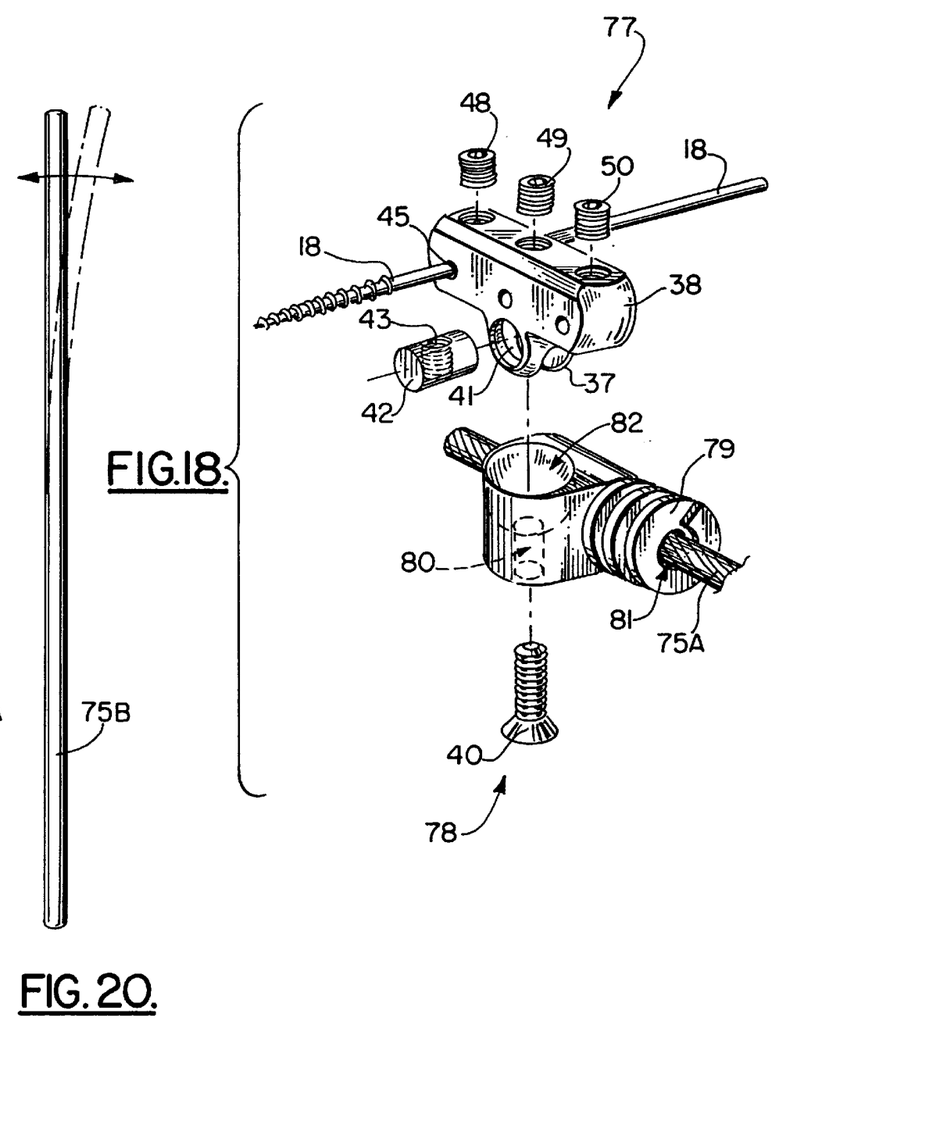
FIG. 18 is a partial perspective exploded view of the alternate embodiment of the apparatus of the present invention.
FIGS. 19–20 are partial perspective view of the alternate embodiment of the apparatus of the present invention illustrating flexible cable and flexible rod portions respectively.
Figure 19:
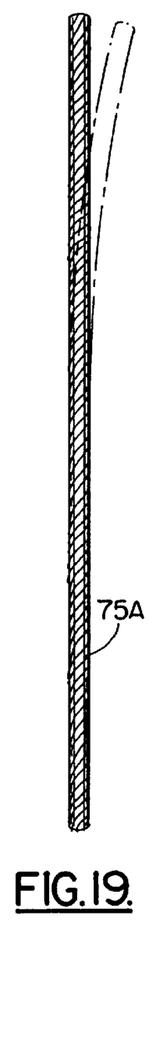

FIGS. 16–20 show an alternate embodiment of the apparatus of the present invention designated generally by the numeral 10A in FIG. 16. As with the preferred embodiment of FIGS. 1–10, fixation apparatus 10A can be attached to a patient's bone tissue such as radius 11, and metacarpals 13 using proximal bone pins 17 and distal bone pins 18.

Proximal clamp 77 and distal clamp 78 (see FIGS. 16–18) interface pins 17, 18 with flexible coupler 76. Flexible coupler 77 includes an elongated coil spring 83 attached at its respective end portions to proximal clamp 78 and distal clamp 78 (see FIGS. 16–17). Each clamp 77, 78 includes a clamp body 79 having an open ended bore 81 for receiving a flexible cable 75A or a flexible rod 75B (see FIGS. 16–17 and 19–20). A pin body 38 attaches to clamp body 79 at concavity 82 using bolt 40. Pin body 38 and its components can be constructed like the pin body 38 shown in FIG. 5 and described herein.

The following table lists the parts numbers and parts descriptions as used herein and in the drawings attached hereto.

| PARTS LIST | |
|---|---|
| Part Number | Description |
| 10 | fixation apparatus |
| 10A | fixation apparatus |
| 11 | radius |
| 12 | wrist |
| 13 | metacarpals |
| 14 | rod |
| 15 | proximal rod section |
| 16 | distal section |
| 17 | proximal bone pin |
| 18 | distal bone pin |
| 19 | flexible rod connector member |
| 20 | cylindrical proximal end |
| 21 | cylindrical distal end |
| 22 | coil spring section |
| 23 | cylindrical bore |
| 24 | arrow |
| 25 | contact point |
| 26 | hemispherical tip |
| 27 | hemispherical tip |
| 28 | proximal clamp |
| 29 | distal clamp |
| 30 | clamp body |
| 31 | flange |
| 32 | flange |
| 33 | gap |
| 34 | C-shaped section |
| 35 | cylindrical bore |
| 36 | hemispherically-shaped opening |
| 37 | hemispherically-shaped projection |
| 38 | pin body |
| 39 | set screw |

-continued

PARTS LIST

| Part Number | Description |
| --- | --- |
| 40 | head |
| 41 | cylindrically-shaped bore |
| 42 | nut |
| 43 | internally threaded bore |
| 44 | threaded shaft |
| 45 | pin bore |
| 46 | pin bore |
| 47 | pin bore |
| 48 | set screw |
| 49 | set screw |
| 50 | set screw |
| 51 | internally threaded opening |
| 52 | internally threaded opening |
| 53 | internally threaded opening |
| 54 | arrow |
| 55 | spring compressor |
| 56 | beam |
| 57 | tab |
| 58 | socket |
| 59 | hexagonal bore |
| 60 | adjustable spring compressor |
| 61 | tab |
| 62 | tab |
| 63 | slot |
| 64 | telescoping section |
| 65 | telescoping section |
| 66 | arrow |
| 67 | bolted connection |
| 68 | knee |
| 69 | interface |
| 70 | femur |
| 71 | tibia |
| 72 | gap |
| 73 | guide |
| 74 | guide |
| 75A | flexible cable |
| 75B | flexible rod |
| 76 | flexible coupler |
| 77 | proximal clamp |
| 78 | distal clamp |
| 79 | clamp body |
| 80 | open ended bore |
| 81 | open ended bore |
| 82 | concavity |
| 83 | coil spring |

The foregoing embodiments are presented by way of example only; the scope of the present invention is to be limited only by the following claims.

What is claimed is:

1. An orthopaedic fixation apparatus comprising:
   a) a first rod member having a pair of opposed end portions, at least one of the end portions being generally hemispherically shaped;
   b) a second rod member having end portions, at least one of which is generally hemispherically shaped, the two rods being positioned end-to-end during use with the corresponding hemispherically-shaped portions abutting;
   c) a flexible shaft coupler that forms a connection between the hemispherically shaped respective end portions of the rod members;
   d) a plurality of bone pins for forming connections to first and second bone parts at spaced apart positions generally on opposite sides of the flexible shaft coupler; and
   e) clamps for forming an interface in between each of the bone pins and the rod members.

2. The joint fixation apparatus of claim 1 wherein each of the rod sections is generally linear, having a central longitudinal axis.

3. The joint fixation apparatus of claim 1 wherein the coupler includes a coil spring portion.

4. The apparatus of claim 1 wherein the flexible coupler includes a generally cylindrically-shaped member having a pair of rigid end portions and a flexible central portion.

5. The apparatus of claim 1 wherein there is further provided a coupler retainer for holding the coupler in a fixed rigid position.

6. The apparatus of claim 1 wherein each of the clamps hold multiple bone pins.

7. The apparatus of claim 1 wherein each of the clamps is an articulating clamp that can both rotate and angulate the bone pins relative to one of the rod members.

8. The apparatus of claim 1 wherein the flexible coupler comprises a pair of rigid end portions each having a bore and a flexible coil spring section that is affixed to the respective rigid portions, the combination of the rigid portions and coil spring having a common open-ended bore that receives the rod ends during use.

9. An orthopaedic fixation apparatus for fixating a patient's joint that has a natural flexion comprising:
   a) a first rod member having a pair of opposed end portions;
   b) a second rod member having end portions, the two rods being positioned end-to-end during use;
   c) a flexible shaft coupler that forms a connection between an end portion of the first rod member and an end portion of the second rod member, the coupler having an initial position and being biased to return to the initial position after the patient flexes the joint;
   d) a plurality of bone pins for forming connections to first and second bone parts at spaced apart positions generally on opposite sides of the flexible shaft coupler; and
   e) first and second clamps for forming an interface between the bone pins and the rod members, wherein the combination of the rod sections and flexible shaft coupler enable the clamps to conform to the natural flexion of the joint to avoid possibilities of bone fragment displacement or loss of fracture reduction.

10. The joint fixation apparatus of claim 9 wherein each of the rod members is generally linear, having a central longitudinal axis.

11. The joint fixation apparatus of claim 9 wherein the axes of the rod members are generally aligned during use.

12. The apparatus of claim 9 wherein the flexible coupler includes a generally cylindrically-shaped member having a pair of rigid end portions and a flexible central portion.

13. The apparatus of claim 9 wherein each of the clamps hold multiple bone pins.

14. The apparatus of claim 9 wherein each of the clamps is an articulating clamp that can both rotate and angulate the bone pins relative to one of the members.

15. An orthopaedic fixation apparatus comprising:
   a) a first rod member having a pair of opposed end portions:
   b) a second rod member having end portions, the two rods being positioned end-to-end during use;
   c) a flexible shaft coupler that forms a connection between respective end portions of the rod members wherein the flexible shaft coupler can both angulate and elongate;
   d) a plurality of bone pins for forming connections to first and second bone parts at spaced apart positions generally on opposite sides of the flexible shaft coupler; and
   e) clamps for forming an interface in between each of the bone pins and the rod members, wherein the combination of the rod sections and flexible shaft coupler enable the clamp to conform to the natural flexion of the joint to avoid possibilities of bone fragment displacement or loss of fracture reduction.

16. An orthopaedic fixation apparatus comprising:
   a) a first rod member having a pair of opposed end portions;
   b) a second rod member having end portions, the two rods being positioned end-to-end during use;
   c) a flexible shaft coupler that forms a connection between respective end portions of the rod members wherein the flexible coupler comprises a pair of rigid end portions each having a bore and a flexible spring section that is affixed to the respective rigid end portions, the combination of the rigid end portions and spring section having a common open-ended bore that receives the rod ends during use;
   d) a plurality of bone pins for forming connections to first and second bone parts at spaced apart positions generally on opposite sides of the flexible shaft coupler; and
   e) clamps for forming an interface in between each of the bone pins and the rod members, wherein the combination of the rod sections and flexible shaft coupler enable the clamp to conform to the natural flexion of the joint to avoid possibilities of bone fragment displacement or loss of fracture reduction.

17. The apparatus of claim 16 wherein the flexible coupler has a flexible spring section that is a coil spring.

18. An orthopaedic fixation apparatus for fixating a joint that has a natural axis of rotation comprising:
   a) a first rod member having a pair of opposed end portions;
   b) a second rod member having end portions, the two rods being positioned end-to-end during use;
   c) a flexible shaft coupler that forms a connection between an end portion of the first rod member and an end portion of the second rod member wherein the coupler is configured to generally align the rod members so that an end portion of one rod member abuts and engages an end portion of the other rod member, the coupler having an initial position and being biased to return to the initial position after the patient flexes the joint;
   d) a plurality of bone pins for forming connections to first and second bone parts at spaced apart positions generally on opposite sides of the flexible shaft coupler; and
   e) clamps for forming an interface in between each of the bone pins and the rod members, wherein the combination of the rod members and flexible shaft coupler enable the clamps to conform to the natural flexion of the joint to avoid possibilities of bone fragment displacement or loss of fracture reduction.

19. The orthopaedic fixation apparatus of claim 18 wherein the rod members are maintained in contact at respective rod member end portions when one rod member forms an obtuse angle with the other rod member.

20. An orthopaedic fixation apparatus comprising:
   a) a first rod member having a pair of opposed end portions;
   b) a second rod member having end portions, the two rods being positioned end-to-end during use;
   c) a flexible shaft coupler that forms a connection between respective end portions of the rod members and that generally aligns the rod members so that an end portion of one rod member abuts and engages an end portion of the other rod member;
   d) a plurality of bone pins for forming connections to first and second bone pars at spaced apart positions generally on opposite sides of the flexible shaft coupler; and
   e) bone clamps for forming an interface in between each of the bone pins and the rod members, wherein the combination of the rod sections and flexible shaft coupler enable the clamp to conform to the natural flexion of the joint to avoid possibilities of bone fragment displacement or loss of fracture reduction; and
   f) wherein rod member end portions abut each other during angulation of the flexible shaft coupler.

21. An orthopaedic fixation apparatus comprising:
   a) a first rod member having a pair of opposed end portions;
   b) a second rod member having end portions, the two rods being positioned end-to-end during use, with respective rod end portions abutting, the abutting portions being configured to make contact and prevent loss of distraction of the wrist joint so that the length of the radius is maintained;
   c) a flexible shaft coupler that forms a connection between an end portion of the first rod member and an end portion of the second rod member;
   d) a plurality of bone pins for forming connections to first and second bone parts at spaced apart positions generally on opposite sides of the flexible shaft coupler; and
   e) clamps for forming an interface in between each of the bone pins and the rod members, wherein the combination of the rod members and flexible shaft coupler enable the clamps to conform to the natural flexion joint to avoid possibilities of bone fragment displacement or loss of fracture reduction.

22. The joint fixation apparatus of claim 21 wherein each of the rod sections is generally linear, having a central longitudinal axis.

23. The joint fixation apparatus of claim 21 wherein the coupler includes a coil spring portion.

24. The apparatus of claim 21 wherein the flexible coupler includes a generally cylindrically-shaped member having a pair of rigid end portions and a flexible central portion.

25. The apparatus of claim 21 wherein there is further provided a coupler retainer for holding the coupler in a fixed rigid position.

26. The apparatus of claim 21 wherein each of the clamps hold multiple bone pins.

27. The apparatus of claim 21 wherein each of the clamps is an articulating clamp that can both rotate and angulate the bone pins relative to one of the rod members.

28. The apparatus of claim 21 wherein the flexible coupler comprises a pair of rigid end portions each having a bore and a flexible coil spring section that is affixed to the respective rigid portions, the combination of the rigid portions and coil spring having a common open-ended bore that receives the rod ends during use.

29. An orthopaedic fixation apparatus for fixating a joint that has a natural flexion comprising:
   a) a rod member having a pair of opposed end portions and a mid-portion that is flexible;
   b) a flexible coupler that forms a connection between respective end portions of the rod member;
   c) a plurality of bone pins for forming connections to first and second bone parts at spaced apart positions generally on opposite sides of the flexible coupler; and
   d) clamps for forming an interface in between each of the bone pins and the rod members, wherein the combination of the rod member and flexible shaft coupler enable the clamps to conform to the natural flexion of the joint to avoid possibilities of bone fragment displacement or loss of fracture reduction.

30. The joint fixation apparatus of claim 29 wherein the rod is generally linear, having a central longitudinal axis.

31. The joint fixation apparatus of claim 29 wherein the spring is a coil spring portion.

32. The apparatus of claim 29 wherein the flexible coupler includes a generally cylindrically-shaped member having a pair of rigid end portions and a flexible central portion.

33. The apparatus of claim 29 wherein each of the clamps holds multiple bone pins.

34. The apparatus of claim 29 wherein each of the clamps is an articulating clamp that can both rotate and angulate the bone pins relative to the rod member.

35. The apparatus of claim 29 wherein the flexible coupler comprises a pair of rigid end portions each having a bore and a flexible coil spring section that is affixed to the respective rigid portions, the combination of the rigid portions and coil spring having a common open-ended bore that receives the rod during use.

36. An orthopaedic fixation apparatus for fixating a joint that has a natural flexion comprising:
   a) a rod member having a pair of opposed end portions;
   b) a flexible spring coupler with a bore that forms a connection to the rod member at the bore;
   c) a plurality of bone pins for forming connections to first and second bone parts at spaced apart positions generally on opposite sides of the flexible spring coupler; and
   d) clamps for forming an interface in between each of the bone pins and the rod member, wherein the combination of the rod member and flexible shaft coupler enable the clamps to conform to the natural flexion of the joint to avoid possibilities of bone fragment displacement or loss of fracture reduction.

37. An orthopaedic fixation apparatus comprising:
   a) a flexible rod member having a pair of opposed end portions;
   b) a coupler that extends along the rod to form a connection between respective end portions of the rod member the coupler having an initial position and being biased to return to the initial position after the patient flexes the joint;
   c) a plurality of bone pins for forming connections to first and second bone parts at spaced apart positions generally on opposite sides of the flexible shaft coupler; and
   d) clamps for forming an interface in between each of the bone pins and the rod, wherein the combination of the flexible rod and coupler enable the bone clamps to conform to the natural flexion of the joint to avoid possibilities of bone fragment displacement or loss of fracture reduction.

* * * * *